(12) United States Patent
Van Der Schaaf et al.

(10) Patent No.: US 7,538,136 B2
(45) Date of Patent: May 26, 2009

(54) CRYSTALLINE FORMS OF ATORVASTATIN

(75) Inventors: Paul Adriaan Van Der Schaaf, Allschwil (CH); Fritz Blatter, Reinach (CH); Martin Szelagiewicz, Münchenstein (CH); Kai-Uwe Schöning, Windisch (CH)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/130,197

(22) PCT Filed: Dec. 19, 2001

(86) PCT No.: PCT/EP01/15012

§ 371 (c)(1),
(2), (4) Date: Oct. 7, 2002

(87) PCT Pub. No.: WO02/051804

PCT Pub. Date: Jul. 4, 2002

(65) Prior Publication Data

US 2003/0114686 A1 Jun. 19, 2003

(30) Foreign Application Priority Data

Dec. 27, 2000 (EP) .................................. 00811249

(51) Int. Cl.
*A61K 31/40* (2006.01)
*C07D 207/325* (2006.01)

(52) U.S. Cl. ........................................ 514/423; 548/537

(58) Field of Classification Search ............... 548/537; 514/423
See application file for complete search history.

(56) References Cited

U.S. PATENT DOCUMENTS

| | | | | |
|---|---|---|---|---|
| 5,273,995 A | | 12/1993 | Roth | 514/422 |
| 5,298,627 A | | 3/1994 | Butler et al. | 548/517 |
| 5,686,104 A | * | 11/1997 | Mills et al. | 424/451 |
| 5,969,156 A | * | 10/1999 | Briggs et al. | 548/537 |
| 6,121,461 A | * | 9/2000 | McKenzie | 548/530 |
| 2004/0220255 A1 | * | 11/2004 | Schaaf et al. | 514/423 |

FOREIGN PATENT DOCUMENTS

| | | |
|---|---|---|
| WO | 97/03958 | 2/1997 |
| WO | 97/03959 | 2/1997 |
| WO | 97/03960 | 2/1997 |
| WO | 01/36384 | 5/2001 |
| WO | 01/44181 | 6/2001 |
| WO | 02/41834 | 5/2002 |
| WO | 02/43732 | 6/2002 |
| WO | 02/057228 | 7/2002 |
| WO | 02/057229 | 7/2002 |
| WO | 02/059087 | 8/2002 |
| WO | 02/072073 | 9/2002 |

OTHER PUBLICATIONS

Concise Encyclopedia Chemistry (1993) Walter de Gruyter Berlin-New York.*
A. Maureen Rouhi, Chemical & Engineering News, Feb. 24, 2003, pp. 32-35.*
Haleblian et al. Journal of Pharmaceutical Sciences, Aug. 1969, vol. 58, No. 8, pp. 911-929.*
U.S. Pharmacopia #23, National Formulary # 18 (1995), pp. 1843-1844.*
Brittain "polymorphism in pharmaceutical solids" Marcel Dekker, p. 1, 2, 178-179, 185, 219 and 236 (1999).*
US Pharmacopia#23, national formulary #18, p. 1843-1844 (1995).*
Byrn et al. "Solid-State Chemistry of Drugs" (1999), pp. 62-63.*
P. Brower et al., Tetrahedron Letters, vol. 33, No. 17, pp. 2279-2282 (1992).
K. Baumann et al., Tetrahedron Letters, vol. 33, No. 17, pp. 2283-2284 (1992).
Drugs of the Future (1997), vol. 22, No. 9, pp. 956-968.
Guillory, J. K., "Generation of Polymorphs, Hydrates, Solvates, and Amorphous Solids," Chapter 5 in *Polymorphism in Pharmaceutical Solids*, Brittain, H. G., Ed., vol. 95 of *Drugs and the Pharmaceutical Sciences*, Marcel Dekker, Inc., New York, NY, 1999, pp. 183-226.
David J. W. Grant, *Theory and Origin of Polymorphism*, in *Drugs of the Pharmaceutical Sciences*, vol. 95, *Polymorphism in Pharmaceutical Solids*, Chapter 1, (Harry G. Brittain ed., 1999).
Bernstein, J., *Polymorphism in Molecular Crystals, IUCR Monographs on Crystallography* 14 Oxford Science Publications, 2002, pp. 1-28 and 240-256.

* cited by examiner

*Primary Examiner*—Rebecca L Anderson
(74) *Attorney, Agent, or Firm*—Kenyon & Kenyon LLP

(57) ABSTRACT

The present invention is directed to new crystalline forms of Atorvastatin calcium (2:1), referred to hereinafter as polymorphic Forms X, A, B1, B2, C, D and E. Furthermore, the present invention is directed to processes for the preparation of these crystalline forms and pharmaceutical compositions comprising the crystalline forms.

6 Claims, 7 Drawing Sheets

Figure 2: Atorvastatin calcium salt crystal form A

Figure 5: Atorvastatin calcium salt crystal form D

CRYSTALLINE FORMS OF ATORVASTATIN

This application is the U.S. national stage application under 35 U.S.C. §371 of International Patent Application No. PCT/EP01/15012, having an international filing date of Dec. 19, 2001, and claims priority under 35 U.S.C. §119 from European Patent Application No. 00811249.2, filed Dec. 27, 2000.

The present invention is directed to crystalline forms of Atorvastatin calcium, processes for their preparation and pharmaceutical compositions comprising these crystalline forms.

The present invention relates to crystalline forms of Atorvastatin calcium. Atorvastatin calcium is known by the chemical name, [R—(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid calcium salt (2:1). Atorvastatin has the following formula:

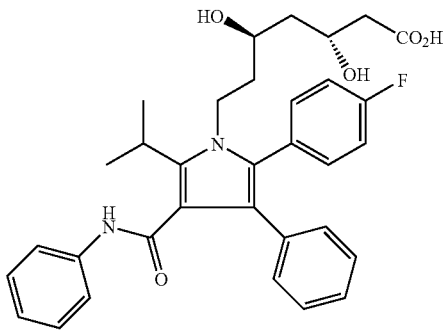

Atorvastatin calcium is an orally-active hypocholesterolaemic, a liver-selective HMG-CoA reductase inhibitor. Processes for the preparation of Atorvastatin calcium are described in U.S. Pat. No. 5,298,627, U.S. Pat. No. 5,273,995 and WO-A-97/03960, and publications by P. L. Brower et al. in Tetrahedron Letters (1992), vol. 33, pages 2279-2282, K. L. Baumann et al. in Tetrahedron Letters (1992), vol. 33, pages 2283-2284 and A. Graul et al. in Drugs Future (1997), vol. 22, pages 956-968.

This calcium salt (2:1) is desirable since it enables Atorvastatin calcium to be conveniently formulated. The processes in the above mentioned patents and publications result in the preparation of amorphous Atorvastatin calcium.

The preparations of Atorvastatin calcium (2:1) described in WO-A-97/03958 and WO-A-97/03959 result in the isolation of crystalline Atorvastatin calcium with the polymorphic forms III, and I, II, and IV, respectively. However, there is still a need to produce Atorvastatin calcium in a reproducible, pure and crystalline form to enable formulations to meet exacting pharmaceutical requirements and specifications. Furthermore, it is economically desirable that the product is stable for extended periods of time without the need for specialised storage conditions.

Surprisingly, there have now been found several novel crystalline forms of Atorvastatin calcium salt (2:1), herein designated as Form X, Form A, Form B1, Form B2, Form C, Form D and Form E. The novel forms of the present invention have a good thermal stability and/or good solubility characterisitics.

Accordingly, the present invention is directed to the following polymorphic Forms X, A, B1, B2, C, D and E of Atorvastatin calcium salt (2:1).

A crystalline polymorph of [R—(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid calcium salt which exhibits a characteristic X-ray powder diffraction pattern with characteristic peaks expressed in d-values (Å) at 27.9 (s), 20.9 (w), 18.9 (w), 16.1 (w), 11.1 (m), 10.5 (m), 9.1 (m), 5.53 (m), 5.07 (w), 4.77 (vw), 4.55 (m), 4.13 (w), 3.69 (w);

herein designated as Form X. Here and in the following the abbreviations in brackets mean: (vs)=very strong intensity; (s)=strong intensity; (m)=medium intensity; (w)=weak intensity; (vw)=very weak intensity.

A crystalline polymorph of [R—(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid calcium salt which exhibits a characteristic X-ray powder diffraction pattern with characteristic peaks expressed in d-values (Å) at 31.0 (vw), 18.6 (m), 17.0 (w), 15.3 (vw), 12.8 (w), 11.2 (m), 9.6 (s), 9.3 (w), 8.6 (w), 7.4 (m), 6.5 (vw), 6.2 (vw), 5.47 (w), 5.21 (m), 4.64 (vs), 4.46 (s), 4.14 (m), 3.97 (m), 3.74 (m), 3.62 (vw), 3.38 (w), 3.10 (m), herein designated as Form A.

A crystalline polymorph of [(R—(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid calcium salt which exhibits a characteristic X-ray powder diffraction pattern with characteristic peaks expressed in d-values (Å) at 27.9 (m), 17.0 (m), 14.2 (w), 12.1 (vs), 10.1 (s), 8.6 (m), 7.1 (m), 6.1 (vw), 5.27 (m), 4.89 (m), 4.68 (m), 4.46 (m), 4.22 (m), 3.90 (w), 3.70 (w), 2.36 (vw), herein designated as Form B1.

A crystalline polymorph of [(R—(R*,R*)]-2-(4-fluorophenyl)-beta,delta-dihydroxy-5-(1-methylethyl)-3-phenyl-4-[((phenylamino)carbonyl]-1H-pyrrole-1-heptanoic acid calcium salt which exhibits a characteristic X-ray powder diffraction pattern with characteristic peaks expressed in d-values (Å) at 28.1 (m), 17.2 (m), 14.0 (vw), 12.3 (s), 10.4 (s), 8.6 (m), 7.5 (w), 7.0 (m), 5.28 (m), 4.88 (m), 4.55 (m), 4.27 (m), 3.88 (vw), 3.73 (m), herein designated as Form B2.

A crystalline polymorph of [R—(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid calcium salt which exhibits a characteristic X-ray powder diffraction pattern with characteristic peaks expressed in d-values (Å) at 28.8 (m), 24.0 (m), 17.1 (m), 11.3 (s), 9.8 (vw), 8.3 (w), 7.7 (vw), 6.9 (vw), 5.64 (vw), 5.21 (w), 4.59 (m), 4.39 (w), 4.16 (w), 3.70 (w), herein designated as Form C.

A crystalline polymorph of [R—(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid calcium salt which exhibits a characteristic X-ray powder diffraction pattern with characteristic peaks expressed in d-values (Å) at 33.7 (w), 31.0 (m), 16.9 (m), 10.3 (s), 7.7 (w), 6.4 (vw), 4.84 (s), herein designated as Form D.

A crystalline polymorph of [R—(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid calcium salt which exhibits a characteristic X-ray powder diffraction pattern with characteristic peaks expressed in d-values (Å) at 26.8 (s), 9.4 (w), 4.6 (m)

herein designated as Form E.

A discussion of the theory of X-ray powder diffraction patterns can be found in "X-ray diffraction procedures" by H. P. Klug and L. E. Alexander, J. Wiley, New York (1974).

Furthermore, the present invention is directed to processes for the preparation of Form X, Form A, Form B1, Form B2, Form C, Form D and Form E.

Form X can generally be prepared by drying of a solution of Atorvastatin calcium in an organic solvent. Examples of such organic solvents are alcohols, like methanol. Preferably, the solution in addition contains an organic non-solvent, like ethers, for example methyl tert.-butyl ether. Drying can be carried out at elevated temperature, or, preferably, at ambient temperature. If desired, during the preparation process seeding with Form X can be carried out.

Form A can generally be prepared by suspending Form X or the amorphous form in an organic solvent, like an alcohol, especially isopropanol. It is preferred that the organic solvent contains as a further solvent some water. The amount of water is preferably about 0.1 to 5%, preferably about 0.5 to 2%, especially about 1% by volume of the suspension. It is preferred that the suspension is treated at temperatures between 10 and 60° C. (preferably 30 to 50° C.), especially for a longer period of time, like 10 to 40 hours. If desired, during the preparation process seeding with Form A can be carried out.

Form A can also be prepared from Atorvastatin lacton upon subsequent reaction with NaOH to form Atorvastatin sodium followed by reaction with $CaCl_2$ in an organic solvent, like an alcohol, especially isopropanol. It is prefered that the organic solvent contains as a further solvent some water. The amount of water is preferably 0.1 to 10%. If desired, during the preparation process seeding with Form A can be carried out.

Form A can also be prepared directly from Atorvastatin lactone upon reaction with $Ca(OH)_2$ in an organic solvent, like an alcohol, especially isopropanol. It is prefered that the organic solvent contains as a further solvent some water. The amount of water is preferably 0.1 to 10%. If desired, during the preparation process seeding with Form A can be carried out.

Form A can also be prepared by the reaction of Atorvastatin ammonium salt with Ca(II)-acetate in an organic solvent or a mixture of organic solvents, preferably a mixture of tert-butyl methyl ether (TBME) and isopropanol. The solid formed in this reaction is isolated by filtration and than stirred as a suspension in an organic solvent, like an alcohol, especially isopropanol. It is prefered that the organic solvent contains as a further solvent some water. The amount of water is preferably 0.1 to 10%. It is prefered that the suspension is treated at temperatures between 10 and 60° C., especially for a longer period of time, like 10 to 60 hours. If desired, during the preparation process seeding with Form A can be carried out.

Form B1 can generally be prepared by suspending Form X or the amorphous form in acetonitrile containing a further organic solvent, like tetrahydrofuran. It is prefered that the suspension is treated at temperatures between 10 and 50° C. (preferably ambient temperature), especially for a longer period of time, like 10 to 40 hours. If desired, during the preparation process seeding with Form B1 can be carried out.

Form B2 can generally be prepared by suspending Form X or the amorphous form in acetonitrile, preferably pure acetonitrile. It is preferred that the suspension is treated at temperatures between 10 and 50° C. (preferably 30 to 50° C.), especially for a longer period of time, like 10 to 40 hours. If desired, during the preparation process seeding with Form B2 can be carried out.

Form C can generally be prepared by suspending Form X or the amorphous form in a mixture of isopropanol and water, and treating the suspension at ambient temperature for a longer period of time, like 10 to 40 hours. If desired, during the preparation process seeding with Form C can be carried out.

Form D can generally be prepared by suspending Form X or the amorphous form in a mixture of ethanol and water at temperatures between about 20 to 60° C. for a longer period of time, like 10 to 40 hours. If desired, during the preparation process seeding with Form D can be carried out.

Form E can generally be prepared by evaporation of a solution of any form of Atorvastatin, preferably Form X, in 2-butanone or from solvent mixtures of 2-butanone with heptane or ethylacetate or ternary mixtures of 2-butanone, heptane and ethylacetate. Evaporation is preferably carried out slowly, for example within 10 to 40 hours. Another object of the present invention are pharmaceutical compositions comprising an effective amount of crystalline polymorphic Form X, Form A, Form B1, Form B2, Form C, Form D or Form E, and a pharmaceutically acceptable carrier.

The polymorphic forms may be used as single components or mixtures.

As to the novel polymorphic forms of Atorvastatin calcium it is preferred that these contain 25-100% by weight, especially 50-100% by weight, of at least one of the novel forms, based on the total amount of Atorvastatin calcium. Preferably, such an amount of the novel polymorphic forms of Atorvastatin calcium is 75-100% by weight, especially 90-100% by weight. Highly preferred is an amount of 95-100% by weight.

The following Examples illustrate the invention in more detail. Temperatures are given in degrees Celsius.

EXAMPLE 1

Preparation of Polymorphic Form X

Atorvastatin calcium Form X is prepared by dissolving 127 mg Atorvastatin calcium in a mixture of 2.0 ml methanol and 6.0 ml methyl tert.-butyl ether and drying of the solution at ambient temperature. Form X is characterized by a x-ray powder diffraction pattern as shown in FIG. 1. Differential scanning calorimetry in a closed sample pan sealed after equilibrium under dry nitrogen for about 16 hours at ambient temperature shows a melting point of 168° C. and an enthalpy of fusion of about 27 J/g (see FIG. 6). Form X if stored under normal conditions contains about 4% of water.

EXAMPLE 2

Preparation of Polymorphic Form A

Form A is prepared by suspending 100 mg of Form X in 3.0 ml isopropanol together with 50 µl $H_2O$ and stirring of this suspension at 40° C. After 9 hours an additional amount of 50 µl of water is added to the suspension and stirring is continued at 40° C. for another 20 hours. The suspension is filtrated and crystalline Form A is obtained. Form A is characterized by a x-ray powder diffraction pattern as shown in FIG. 2. Differential scanning calorimetry of Form A in a closed sample pan sealed after equilibration under dry nitrogen for about 16 hours at ambient temperature reveals a melting point of 179° C. and an enthalpy of fusion of 53 J/g (see FIG. 6).

In the above example it is also possible to start from the amorphous form of Atorvastatin calcium instead of Form X.

EXAMPLE 3

Preparation of Polymorphic Form B1

Atorvastatin calcium crystal Form B1 is prepared by suspending 145 mg of Atorvastatin calcium Form X in a mixture of 1.0 ml acetonitrile and 1.0 ml of tetrahydrofuran at ambient temperature. While the cap of the reaction vial is left open some of the tetrahydrofuran evaporates which leads to a slow reduction of the solubility of Atorvastatin calcium in the system. After 3.5 hours an additional amount of 1.0 ml of acetonitrile is added to the reaction container and stirring is continued for about 15 hours at ambient temperature. After filtration of the suspension crystal form B1 is obtained. Form B1 is characterized by a x-ray powder diffraction pattern as shown in FIG. 3.

In the above example it is also possible to start from the amorphous form of Atorvastatin calcium instead of Form X.

EXAMPLE 4

Preparation of Polymorphic Form B2

Form B2 is prepared by suspending 117 mg of Atorvastatin calcium Form X in 2.0 ml of acetonitrile and stirring this suspension at 40° C. for about 18 hours. In order to reduce the viscosity of the suspension 1.0 ml of acetonitrile is added at ambient temperature to this suspension after the end of the crystallization process. The obtained product is crystal Form B2 which is characterized by an x-ray powder diffraction pattern as shown in FIG. 3.

In the above example it is also possible to start from the amorphous form of Atorvastatin calcium instead of Form X.

EXAMPLE 5

Preparation of Polymorphic Form C

Form C is prepared by suspending 120 mg of Atorvastatin calcium Form X in a mixture of 3.0 ml isopropanol and 1.0 ml water. After one hour of stirring at ambient temperature 2.0 ml water are added and stirring is continued for 15 hours at the same temperature. After filtration of the suspension crystal Form C is obtained which is characterized by the x-ray diffraction pattern as shown in FIG. 4.

In the above example it is also possible to start from the amorphous form of Atorvastatin calcium instead of Form X.

EXAMPLE 6

Preparation of Polymorphic Form D

Form D is prepared by suspending 124 mg of Form X in 3.0 ml of ethanol and by stirring this suspension at ambient temperature. After about 2 hours a suspension of high viscosity is obtained and 1.0 ml of water are added to the suspension, which reduces the viscosity substantially. After addition of water, the temperature is slowly raised to 40° C. and stirring is continued at 40° C. for about 16 hours. After filtration of the suspension crystal Form D is obtained which is characterized by the x-ray diffraction pattern as shown in FIG. 5.

In the above example it is also possible to start from the amorphous form of Atorvastatin calcium instead of Form X.

EXAMPLE 7

Preparation of Polymorphic Form E 60 mg of Atorvastatin Form X are dissolved in 2.0 ml 2-butanone (e.g. Fluka No. 04380) and then 2.0 ml of heptane (e.g. Fluka No. 51745) are added at ambient temperature. This mixture is heated to 50° C. for a few minutes until all solid residues are dissolved. The mixture is then slowly cooled to 5° C. and later equilibrated at ambient temperature. At ambient temperature the solvent is slowly evaporated within about 10 to 20 hours. After complete evaporation of the solvent Atorvastatin Form E is obtained as a solid residue. The X-ray diffraction pattern of Form E is shown in FIG. 7.

EXAMPLE 8

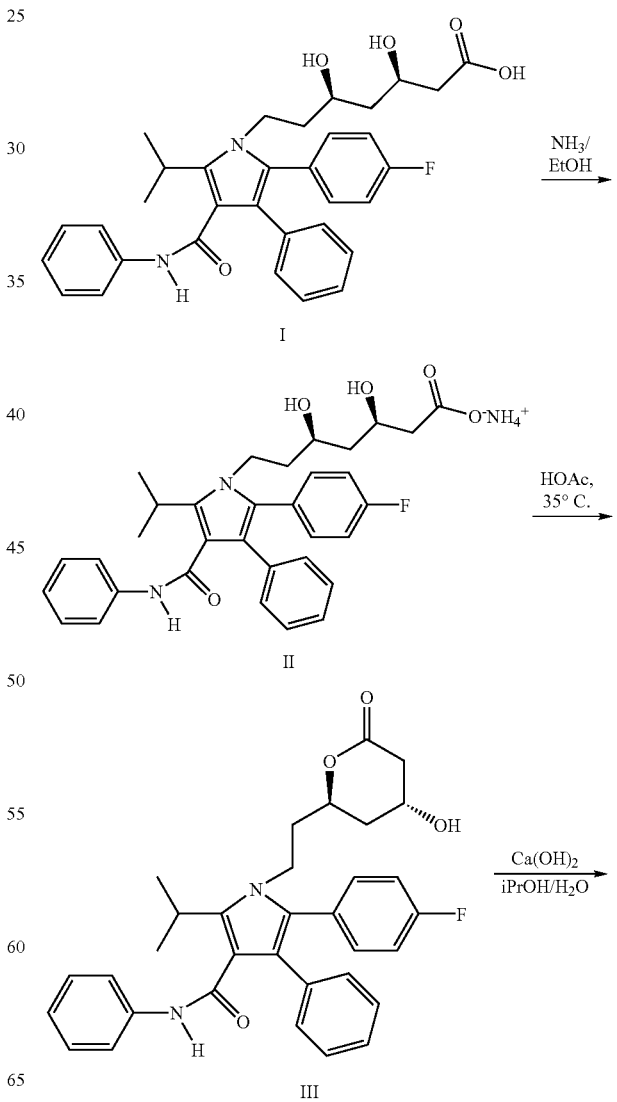

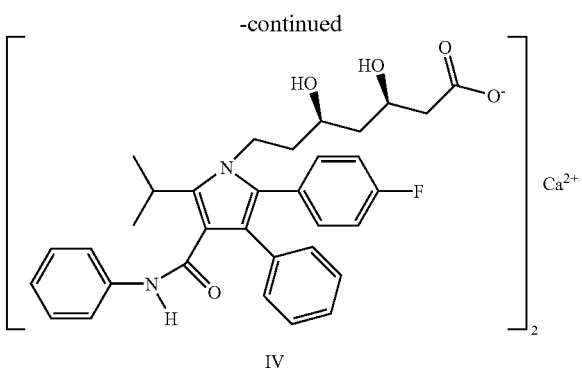

IV a) Preparation of Atorvastatin Lactone III:

Diol acid I (5 g, 8.9 mmol) is dissolved in 10.7 ml ethanol and 5.6 ml 1.6 M $NH_3$ in ethanol ist added at room temperature. The solution is being stirred over 15 to 30 minutes and the solvent is subsequently removed under reduced pressure to give a colorless or slightly beige foam (5.15 g, approximately 100% yield).

Ammonium salt II (23.91 g, 41.7 mmol) is dissolved in 115 ml acetic acid. The yellow solution is being stirred at 35° C. for approximately 16 h. 200 ml dioxane are added twice and the mixture is being concentrated at 40° C. and 35 mbar pressure, respectively. The residue is dissolved in 200 ml TBME and being washing with water and brine and dried over magnesium sulfate. Removal of the solvent affords 21.4 g (approx. 95% yield) Atorvastatin lacton III.

b) Preparation of Atorvastatin Calcium Form A Starting from Atorvastatin Lactone III:

Lacton III (20.6 g, 38.2 mmol) is dissolved in 757 ml 2-propanol/water (19:1) and 1.41 g (0.5 eq) calcium hydroxide is added. The turbid solution is stirred at 40° C. for 3 d whereupon the solution turns into a thick suspension. White crystals of form A are collected by filtration and being dried at 70° C. and 20 mbar pressure overnight. Yield: 19.0 g, 86%.

EXAMPLE 9

Preparation of Atorvastatin Calcium Form A Starting from Atorvastatin Ammonium Salt II Ammonium salt II (2 g, 3.5 mmol) is dissolved in 20 ml TBME/isopropanol (1:2) and a solution of calciumacetat hydrate (0.5 eq) is added dropwise at room temperature. The precipitated calcium salt is collected by filtration and dried at 70° C. and 20 mbar. (Yield 1.6 g, approx. 80%.) The obtained powder is subsequently being stirred in 58 ml 2-propanol/water (19:1) at 40° C. and seeded with 5% crystals of form A. After 4 d Atorvastatin Calcium form A can be collected by filtration (yield 1.5 g, 91%).

Figure 1:
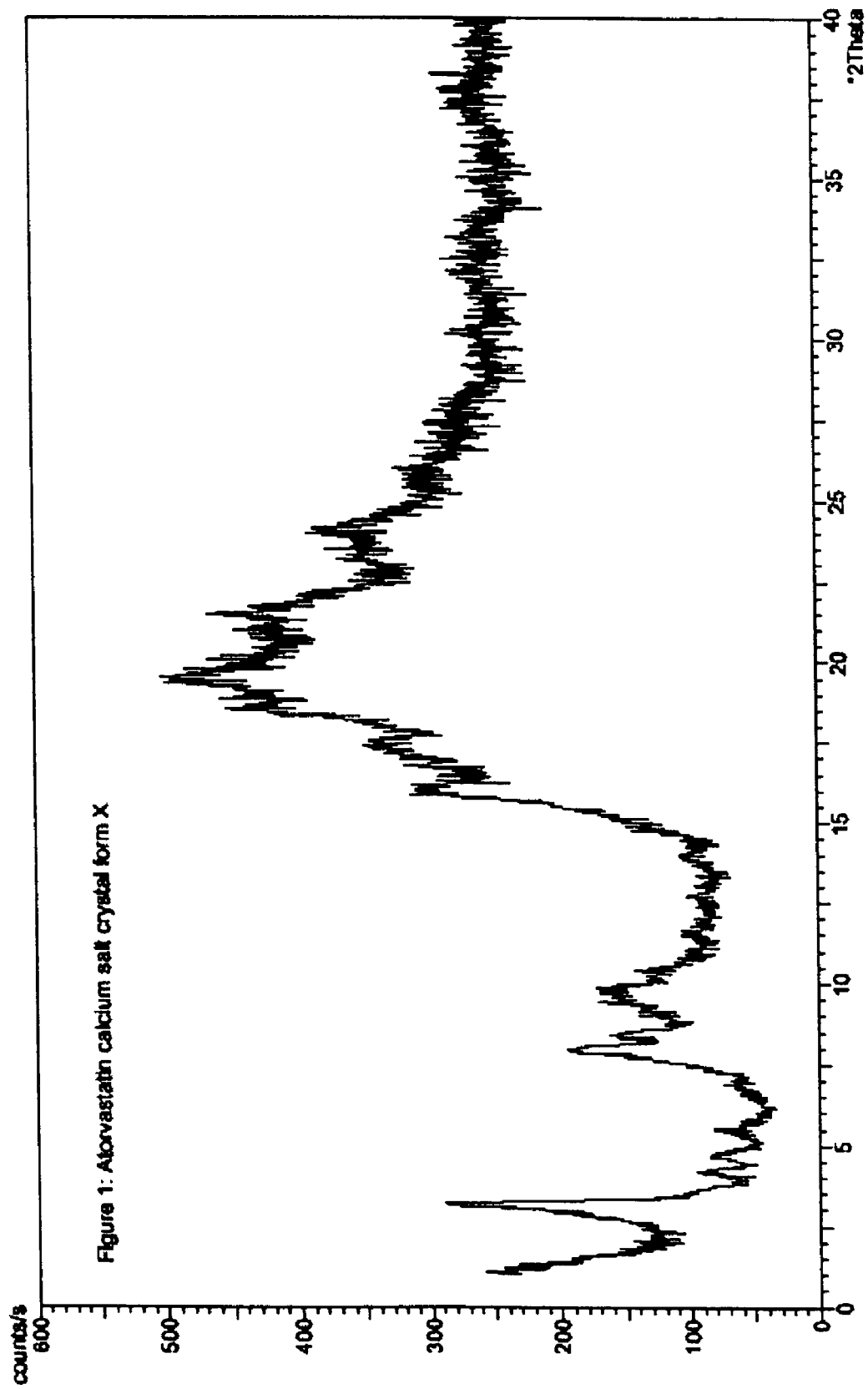
FIG. 1 is a characteristic X-ray powder diffraction pattern for Form X.
Figure 2:
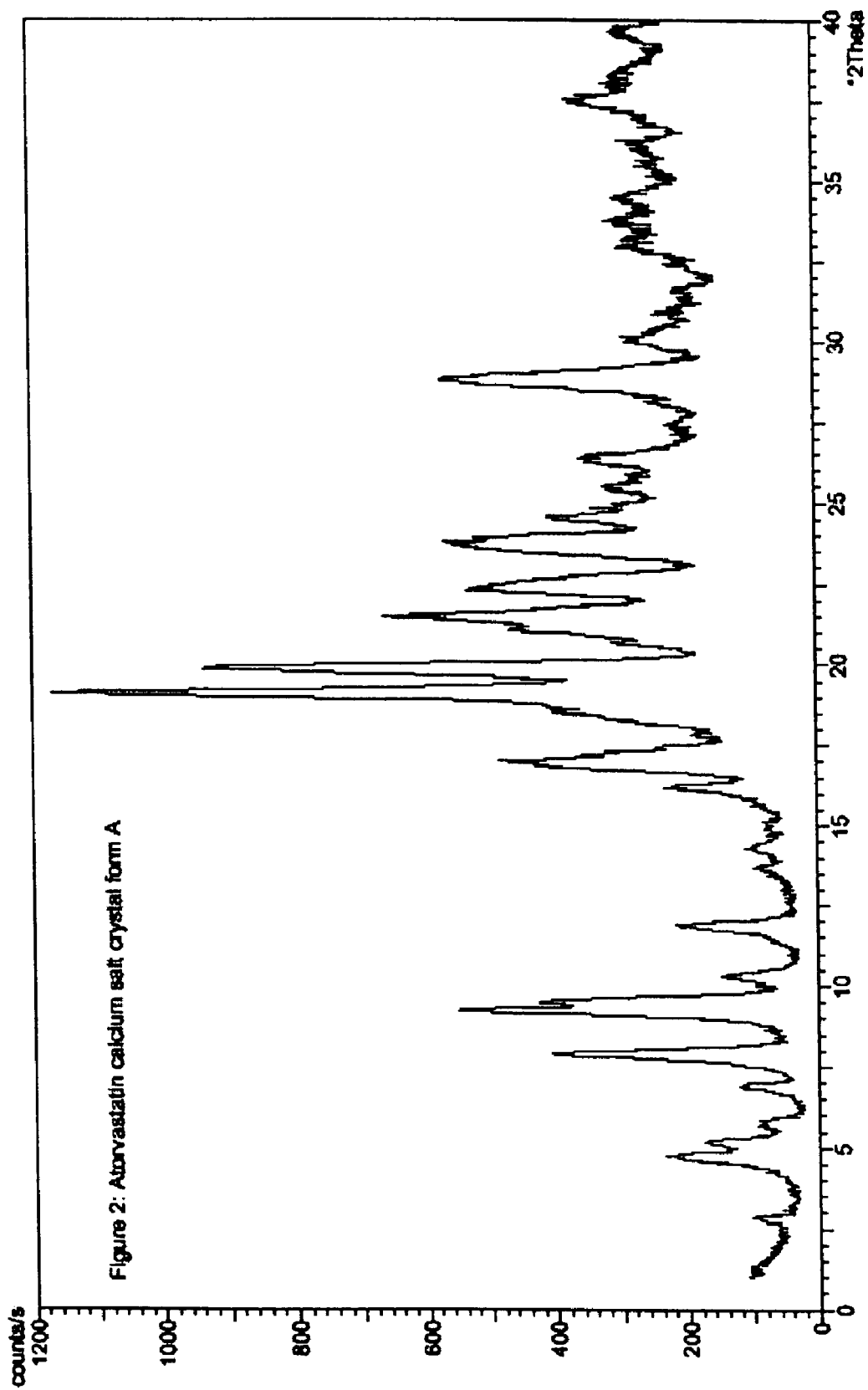
FIG. 2 is a characteristic X-ray powder diffraction pattern for Form A.

The invention claimed is:

1. A crystalline Form X of [R—(R*,R*)]-2-(4-fluorophenyl)-beta,delta-di-hydroxy-5-(1-methylethyl)-3-phenyl-4-[(phenylamino)carbonyl]-1H-pyrrole-1-heptanoic acid calcium salt having the PXRD spectrum substantially as depicted in FIG. 1.

Figure 3:
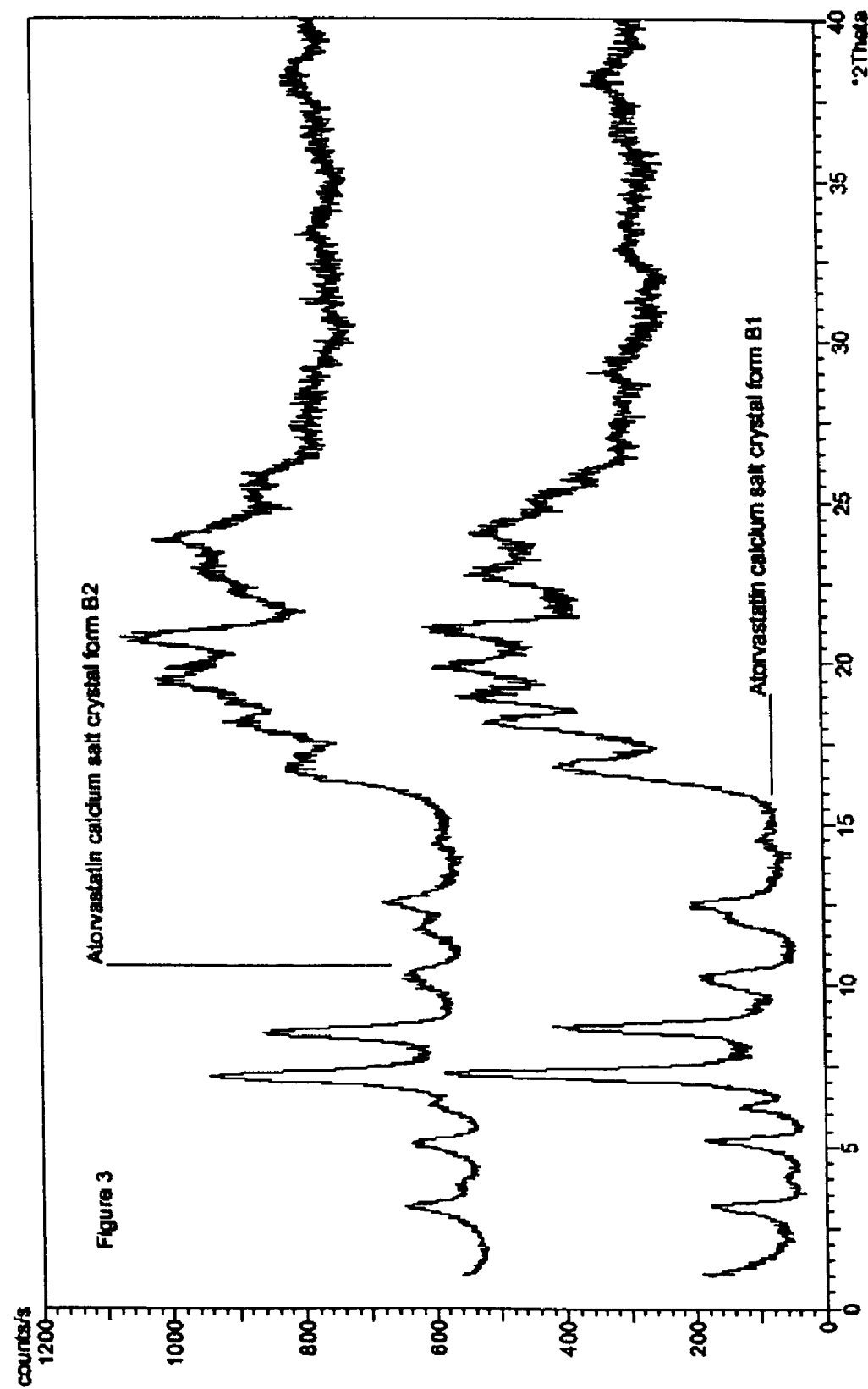
FIG. 3 are characteristic X-ray powder diffraction patterns for Form B1 and B2.

2. A crystalline Form B1 of [R—(R*,R*)]-2-(4-flourophenyl)-beta,delta-di-hydroxy-5-(1-methylethyl)-3-phenyl-4-[(phenylamino)carbonyl]-1H-pyrrole-1-heptanoic acid calcium salt having the PXRD spectrum substantially as depicted in FIG. 3.

3. A crystalline Form B2 of [R—(R*,R*)]-2-(4-flourophenyl)-beta,delta-di-hydroxy-5-(1-methylethyl)-3-phenyl-4-[(phenylamino)carbonyl]-1H-pyrrole-1-heptanoic acid calcium salt having the PXRD spectrum substantially as depicted in FIG. 3.

Figure 4:
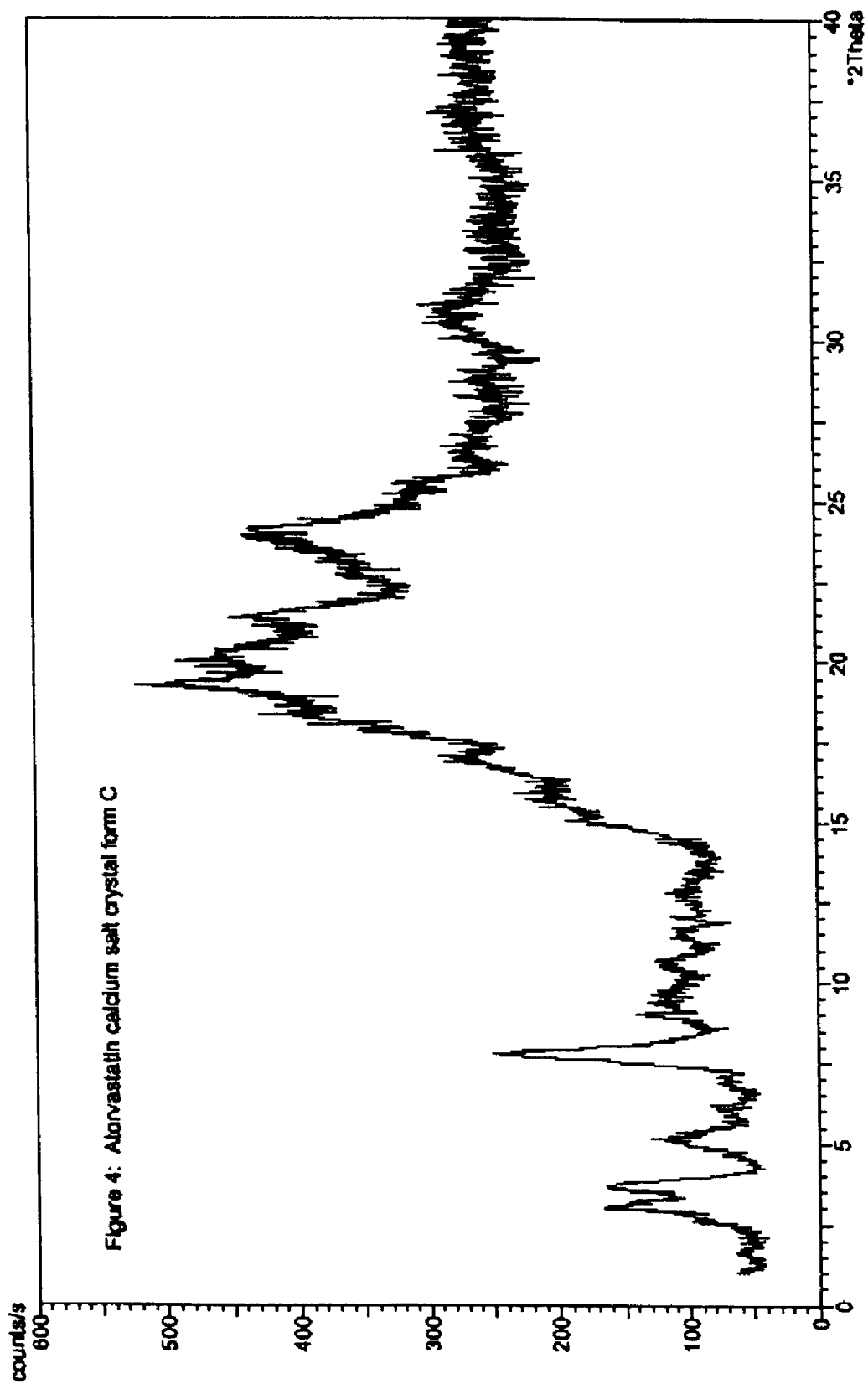
FIG. 4 is a characteristic X-ray powder diffraction pattern for Form C.

4. A crystalline Form C of [R—(R*,R*)]-2-(4-flourophenyl)-beta,delta-di-hydroxy-5-(1-methylethyl)-3-phenyl-4-[(phenylamino)carbonyl]-1H-pyrrole-1-heptanoic acid calcium salt having the PXRD spectrum substantially as depicted in FIG. 4.

Figure 5:
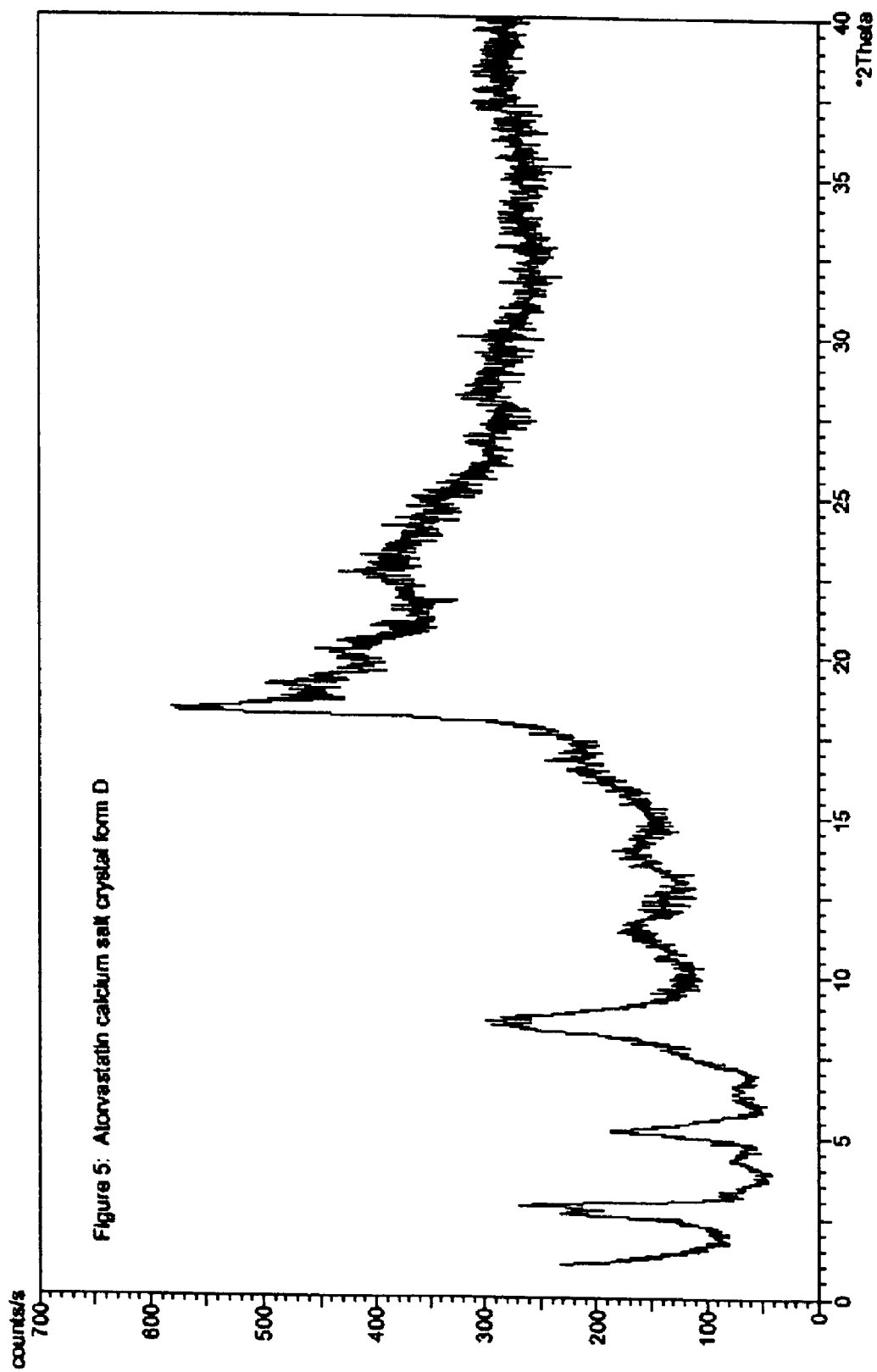
FIG. 5 is a characteristic X-ray powder diffraction pattern for Form D.
Figure 6:
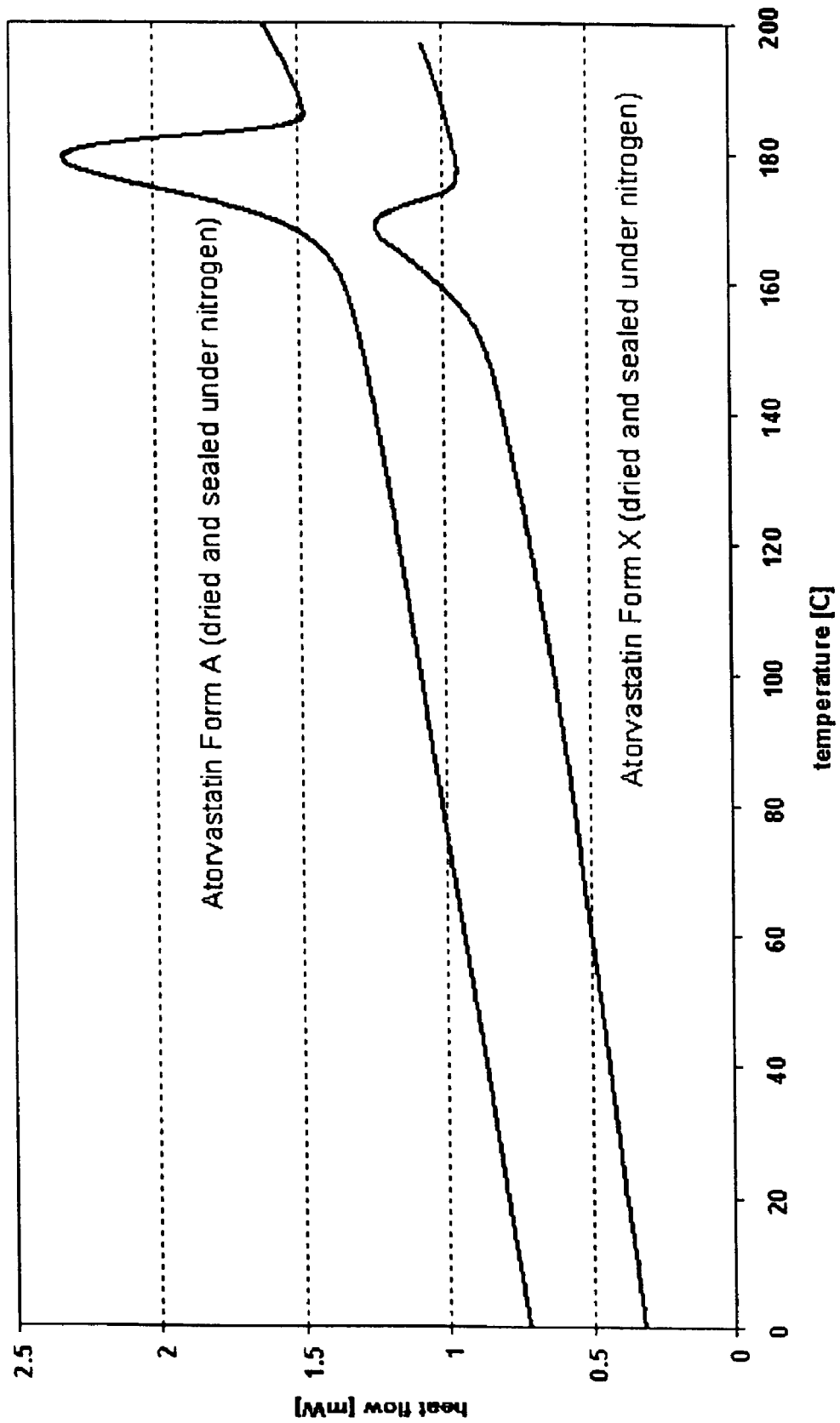
FIG. 6 are characteristic Differential Scanning Calorimetry (DSC) scans of Form A and Form X.

5. A crystalline Form D of [R—(R*,R*)]-2-(4-flourophenyl)-beta,delta-di-hydroxy-5-(1-methylethyl)-3-phenyl-4-[(phenylamino)carbonyl]-1H-pyrrole-1-heptanoic acid calcium salt having the PXRD spectrum substantially as depicted in FIG. 5.

Figure 7:
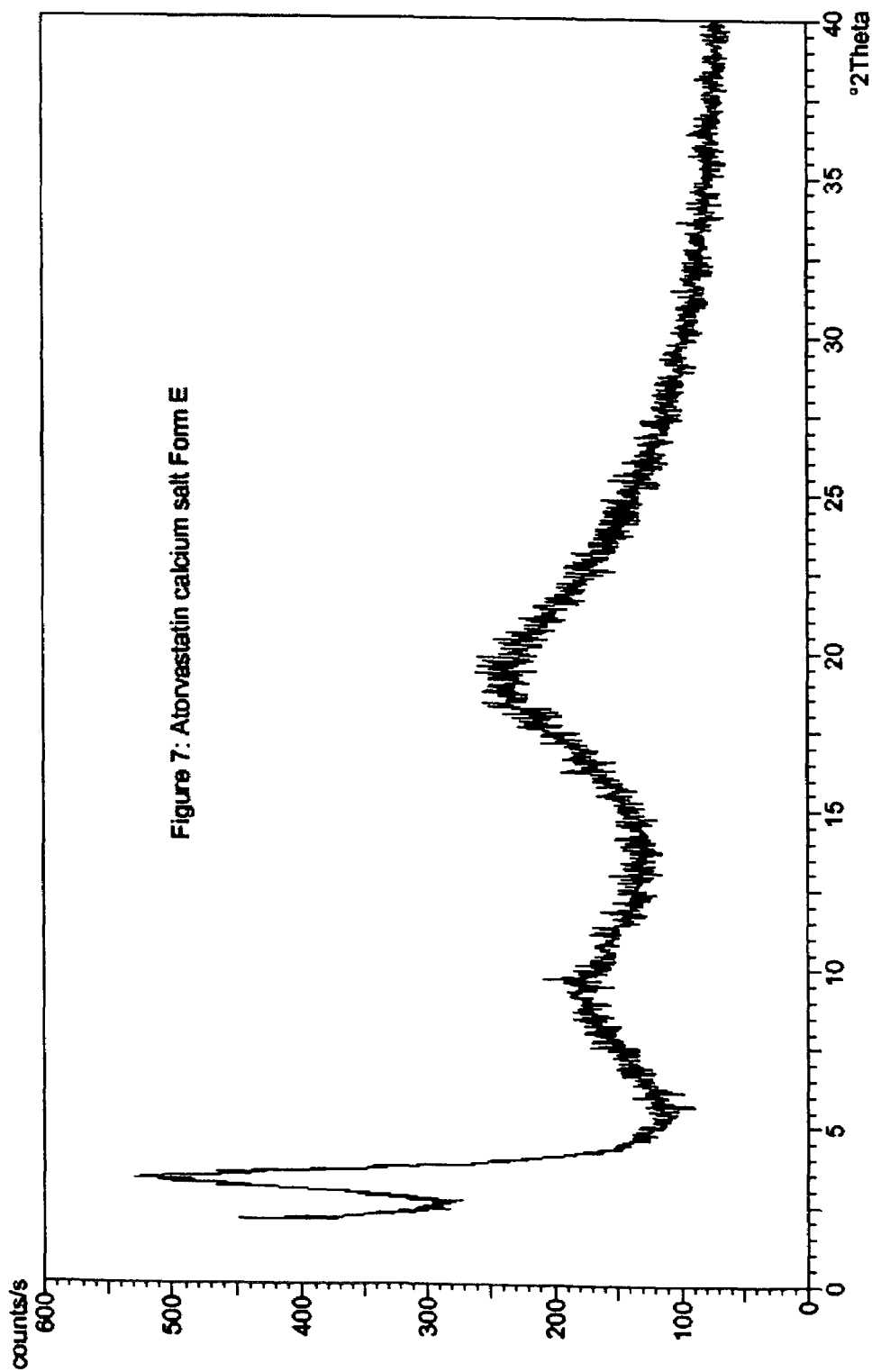
FIG. 7 is a characteristic X-ray powder diffraction pattern for Form E.

6. A crystalline Form E of [R—(R*,R*)]-2-(4-flourophenyl)-beta,delta-di-hydroxy-5-(1-methylethyl)-3-phenyl-4-[(phenylamino)carbonyl]-1H-pyrrole-1-heptanoic acid calcium salt having the PXRD spectrum substantially as depicted in FIG. 7.

* * * * *